United States Patent [19]
Wright et al.

[11] Patent Number: 5,211,180
[45] Date of Patent: May 18, 1993

[54] RESPIRATORY TEST APPARATUS

[75] Inventors: Basil M. Wright, Green; Derek P. Hutchison, Essex, both of England

[73] Assignee: Clement Clarke International Limited, England

[21] Appl. No.: 601,372

[22] Filed: Oct. 23, 1990

[30] Foreign Application Priority Data

Oct. 25, 1989 [GB] United Kingdom ............. 8923982

[51] Int. Cl.⁵ ............................................ A61B 5/093
[52] U.S. Cl. .................................. 128/725; 128/727; 73/861.074; 73/861.071; 73/242
[58] Field of Search .................. 128/725, 727; 73/861.71, 861.74, 242

[56] References Cited

U.S. PATENT DOCUMENTS

| | | | |
|---|---|---|---|
| 2,538,785 | 1/1951 | Korig | 73/861.71 |
| 3,458,565 | 5/1976 | Wright | 128/727 |
| 4,041,935 | 8/1977 | Garbe | 128/727 |
| 4,259,967 | 4/1981 | Vooren et al. | 128/720 |
| 4,444,201 | 4/1984 | Itoh | 128/725 |
| 4,558,710 | 12/1985 | Eichler | 128/725 |
| 5,058,601 | 10/1991 | Riker | 128/725 |

Primary Examiner—William E. Kamm
Assistant Examiner—Brian L. Casler
Attorney, Agent, or Firm—Burns, Doane, Swecker & Mathis

[57] ABSTRACT

A respiratory test apparatus for lung function comprises a chamber into which air can be blown by a subject to displace a piston. The chamber communicates with a space shielded from the incoming air flow to provide a measure of the static air pressure in the chamber, a pressure transducer providing an input of that pressure value a data processor. The data processor is arranged to provide outputs indicative of such functions as a subject's peak respiratory flow rate and the volume of air exhaled.

12 Claims, 3 Drawing Sheets

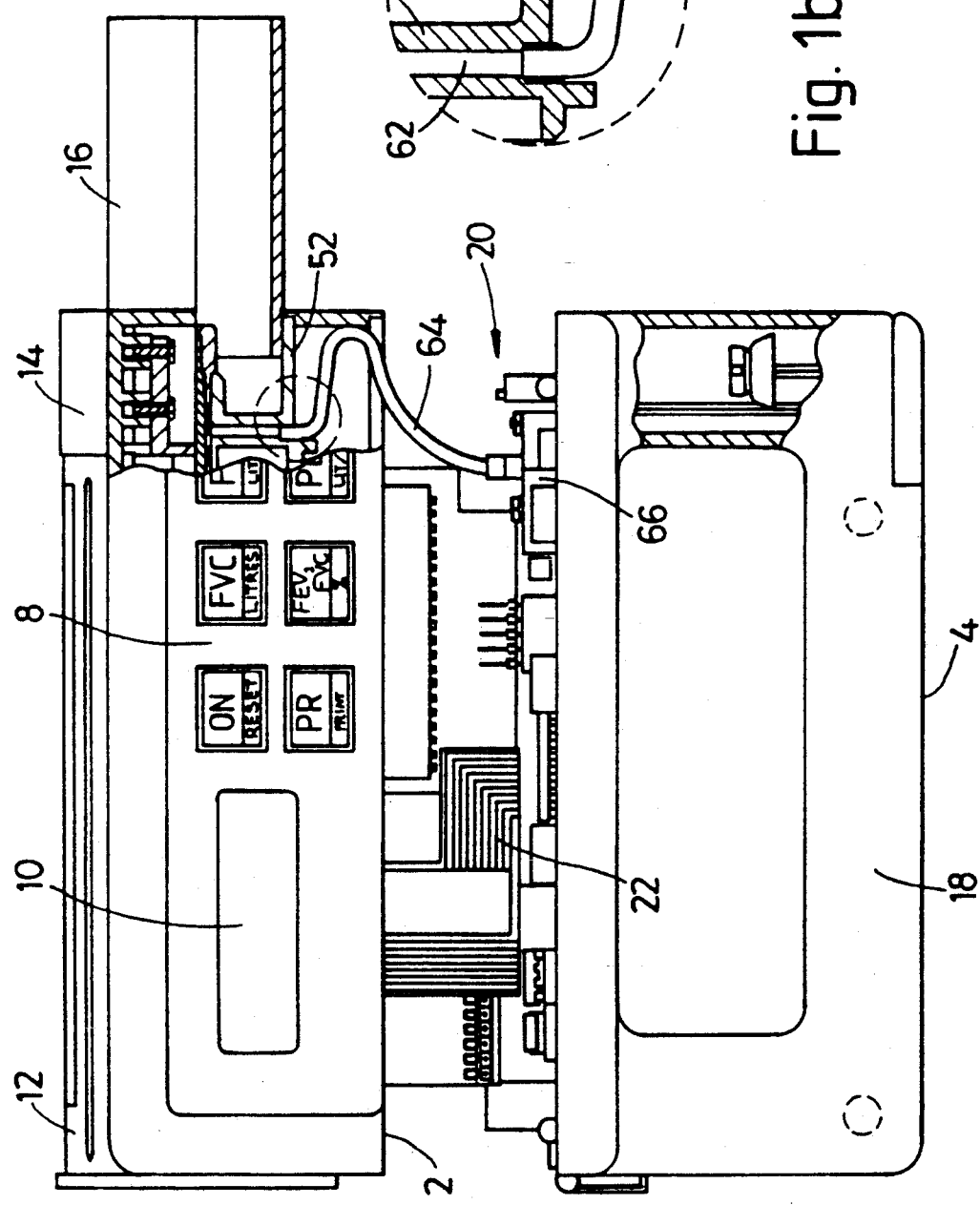
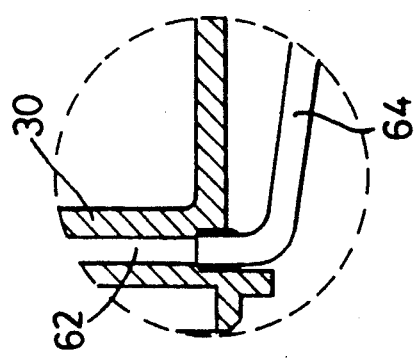

5,211,180

RESPIRATORY TEST APPARATUS

BACKGROUND OF THE INVENTION

This invention relates to apparatus for the measurement of air pressures and/or flows and the like, in particular for medical testing of lung function.

Apparatus is already known (the MiniWright Peak Flowmeter, manufactured by Clement Clarke International Ltd, Harlow, Essex) for measuring the peak flow rate of exhalation, in which the subject blows into a cylindrical measurement container to move a piston in the container against the force of a spring. The displacement of the piston progressively uncovers an open slot in the side of the container along which a pointer is slid by the piston to mark the greatest displacement of the piston and thereby provide a measure of the peak flow rate in the subject's airways.

With appropriate calibration, this apparatus is able to give acceptable comparative results, but its use is limited. It is an object of the present invention to provide an improved instrument, and to provide such an instrument that can produce further data in respiratory testing.

SUMMARY OF THE INVENTION

According to the invention, there is provided respiratory test apparatus comprising a chamber communicating with an entry conduit through which air can be blown into the chamber to escape therefrom at a restricted rate, pressure sensing means for providing a measure of air pressure being arranged to be responsive to the pressure in a region of the chamber shielded from the flow of air through a main interior space between said entry and outlet, and data processing means for the pressure values measured for deriving one or more parameters relating to the respiratory performance of the subject.

The sensed air pressure is preferably tapped from a space that has a restricted connection with a main interior space of the chamber through which said flow of air passes. In one convenient arrangement, the pressure is measured in a region that communicates with the main interior space of the chamber through a passage bounded by a wall extending into said main space away from an opening or openings through which air enters the chamber. If the air entry opening or openings are located in a fixed end wall of the chamber, said passage can be formed by a tubular extension from said end wall into the main interior space.

The data processing means may be arranged to sense the air pressure continuously or at predetermined intervals. Using the sensed values it is possible to determine a number of parameters through appropriate data processing means. It can be arranged that not only peak pressure, but the peak flow rate, the volume of air exhaled (in total or over some predetermined period) and combinations of these parameters are evaluated. It is also possible to obtain a continuous representation or plot of the air pressure in the chamber over the whole exhalation cycle.

An embodiment of the invention will be described in more detail with reference to the accompanying drawings by way of example.

BRIEF DESCRIPTION OF THE DRAWINGS

FIGS. 1a and 2 are partially sectioned side and end views of respiratory test apparatus according to the invention, the two outer casing parts of the apparatus being drawn separated to show some of the internal constructional details, FIG. 1a showing partly sectioned on the line I—I in FIG. 3 and FIG. 1b showing a detailed illustration to a larger scale of a part of its construction.

DESCRIPTION OF THE PREFERRED EMBODIMENT

Figure 2:
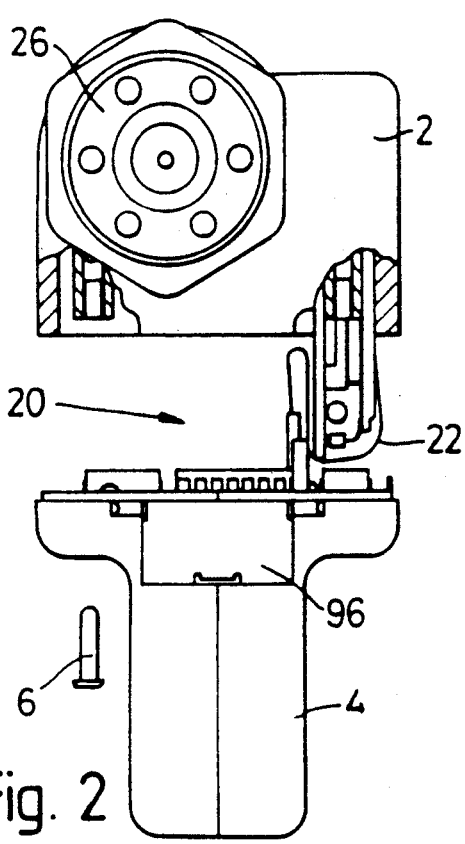
Figure 3:
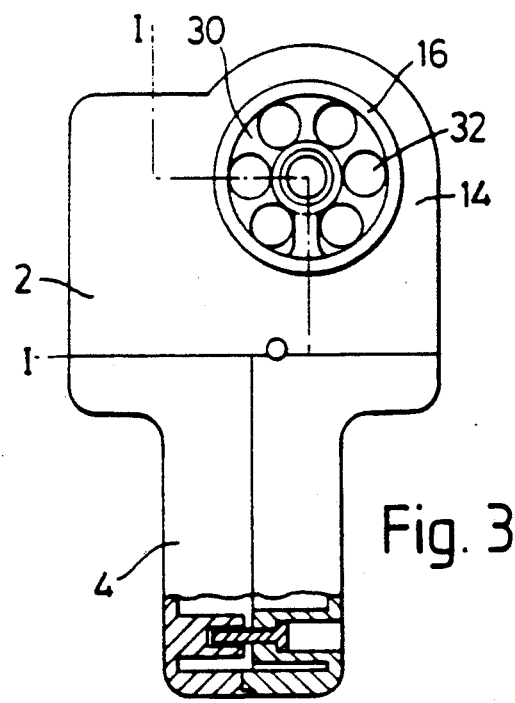
FIG. 3 is an opposite end view of the apparatus, also partly sectioned.
Figure 4:
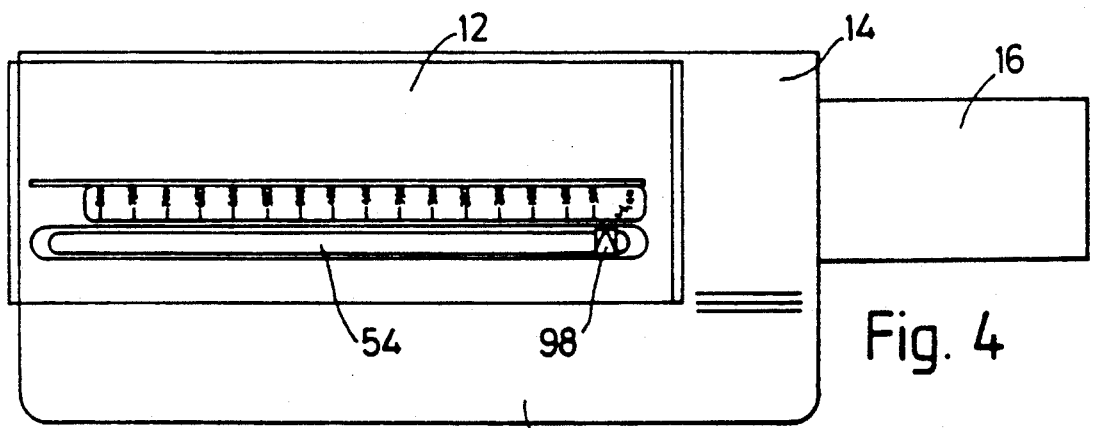
FIGS. 4 and 5 are top and bottom plan views of the apparatus.
Figure 5:
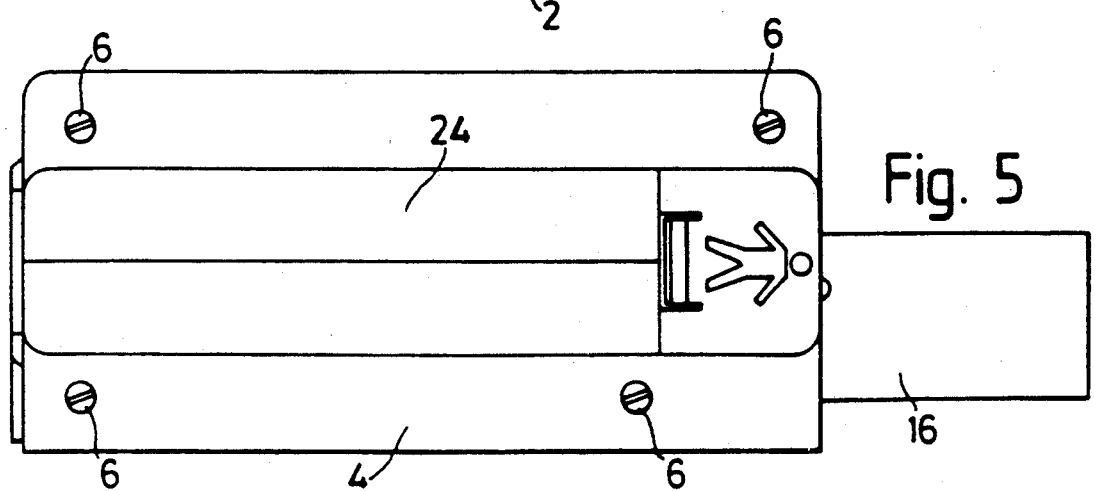

When the apparatus illustrated is in the fully assembled condition, the two outer casing parts 2,4 of the apparatus, shown separated in FIGS. 1 and, 2, are secured together, as shown in FIG. 3, by screws 6 (shown in FIG. 2 only). The upper casing part 2 contains a keypad 8 and a numerical display 10. Mounted in a tubular end portion 14 of the upper casing part is a cylindrical container 12 provided with a removable mouthpiece 16. The lower casing part provides a handle 18 for the apparatus in use and it has a compartment storing batteries (not shown) for its operation. Components of the electronic data processing means 20 are mounted in both parts of the casing in the region of the joint between them and a ribbon cable 22 connects the keypad to this circuit.

Figure 6:
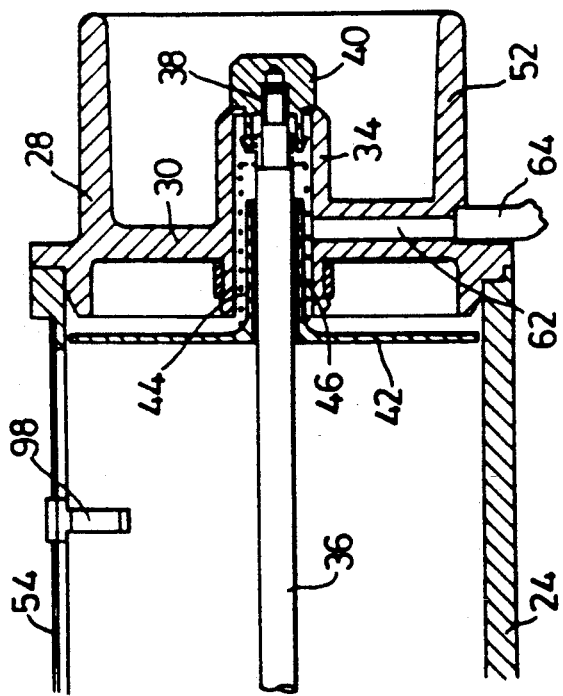
FIG. 6 is a detail sectional view showing the measurement chamber of the apparatus.
Figure 7:
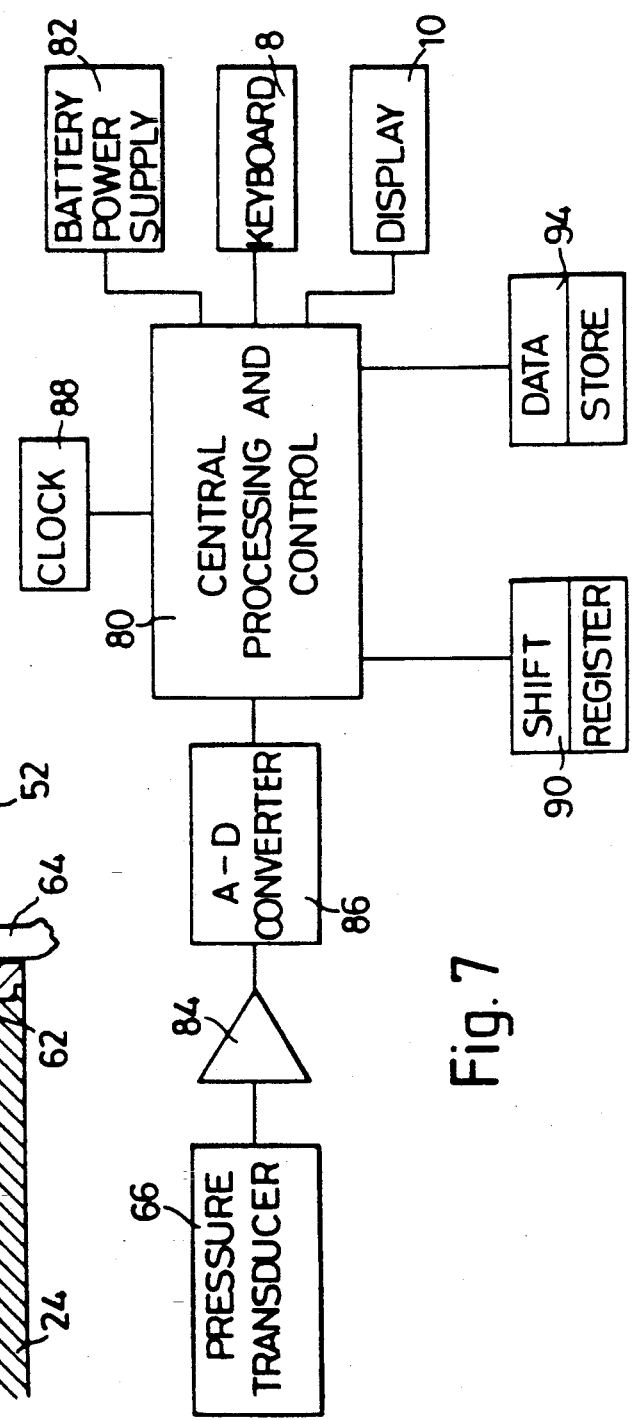
FIG. 7 is a block diagram illustrating the data processing means of the apparatus.

The container 12 mounted in the upper casing part has a moulded cylindrical body 24 integral with one apertured end wall 26. At its other end, a cldsure member 28 is sealingly secured to the body. The member includes an opposite end wall 30 for the interior of the body, and the wall 30 is provided with apertures 32 opening into the body interior. As shown in FIG. 6, integral with the end wall 30 is a central axial sleeve 34 through which extends a rod 36. The rod is secured to the sleeve by a threaded engagement 38 with a press plug 40 in the end of the sleeve that also seals the space within the sleeve from the exterior. A plate piston 42 is mounted slidably, on the rod 36 and has an integral collar 44 having a loose running fit with the rod and maintaining the plate piston perpendicular to the rod. A coil spring 46 is secured at one end to the piston and has its other end held between the rod 36 and the plug 40.

The end wall 30 has an extended collar 52 in which the tubular mouthpiece 16 is a friction fit. When a subject blows into the mouthpiece the air passes into the container through the end wall apertures 32 to a main pressure chamber defined between the end wall 30 and the piston 42. As the subject blows, the pressure of the air forces the piston along the chamber against the force of the spring 46 and past the end of an axial slot 54, which runs almost the full length of the body 24, so allowing air in the pressure chamber to escape. The instantaneous air pressure in the chamber is thus dependent upon the rate of delivery of air into the chamber by the subject and it determines the position of the piston along the chamber.

Formed integrally within the end wall 30 is a radial passage 62, opening at its inner end into the interior of the sleeve 34. At its opposite end, a flexible tube 64 connects the passage to a pressure transducer 66 mounted in the casing lower part 4. The sleeve 34 provides relatively restricted communication between the passage 62 and the main pressure chamber, while the sleeve 34 tends to shield the passage from the currents of air flowing into the chamber. The pressure recorded by the transducer 66 is therefore essentially unaffected by transient disturbances such as arise from turbulence in the air flow through the chamber. The instantaneous static pressure in the chamber is thus measured by the transducer with a greater consistency, the reading being unaffected by how fast air is entering the chamber.

The electronic data processing means 20 for the pressure transducer signals comprise a processing and control unit 80 driven by the supply 82 from the batteries in the lower casing part. The unit 80 is arranged to output measured values to the display 10 by operation of the keys of the keypad 8. The pressure transducer signals are transmitted, through an amplifier 84 and an analogue-digital converter 86, to the control unit 80 where a clock 88 actuates sampling of the digitised pressure signal at an appropriate rate, e.g. at 3 ms intervals. The data sampled is stored by the control unit in a RAM arranged in the form of a shift register 90.

The values of particular interest are the volume of air exhaled in one cycle or forced vital capacity (FEV), which is measured by integrating the pressure value samples with respect to time over the complete exhalation, the forced expiratory volume in the first second (FEV-1), which corresponds to the value of that integral over the first second, and the peak exhalatory flow rate (PEF). To measure PEF, as data samples enter the shift register 90, the latest value is compared there with the earliest values the register carries. Preferably the processing software is able to average stored values and when the latest value exceeds the average of a group of the earliest value by a predetermined amount, ie. when a threshold exhalation pressure rise has been passed, the control unit 20 is triggered to output further values to a data store 94 for processing in the control unit. With appropriate calibration, the instantaneous pressure values can of course also be employed to evaluate the flow rate.

The results of the data processing can be adjusted and scaled as may be appropriate to provide read-out values that are shown on the display using the keypad commands. The apparatus also has a socket (behind a cover 96) to plug into a printer (not shown) onto which the measurement results can be transferred, and may have a further socket (e.g. RS232) to connect with and transfer the data to a computer (in particular a PC).

The data store 94 is arranged to receive data for a set period, e.g. 10 seconds. The store is cleared in preparation for a further test when a rest button on the keypad is pressed. A further control (not shown) monitors the shift register trigger and the operation of the keypad to switch off power if there has been no value triggered to store nor a key pressed for a certain time, e.g. 90 seconds.

The slot 54 has a scale pointer 98 slidably mounted in it to be pushed along the slot by the piston as it is displaced against the force of the spring 46. A direct reading of the peak exhalation flow rate is thus given in the manner of the MiniWright Peak Flowmeter referred to above and can be used comparatively with the electronically evaluated results.

We claim:

1. Respiratory test apparatus comprising a chamber having a main interior space defined between an end wall and a piston, at least one entry opening into said main interior space, a conduit communicating with said main interior space through said at least one entry opening for air to be blown by a subject into the chamber through said conduit, an outlet from the chamber permitting said air blown into said main interior space and to escape therefrom at a restricted rate, pressure sensing means for providing a measure of air pressure, a portion of the chamber being offset from a flow path between said at least one opening and said outlet from the chamber, said offset portion of the chamber being disposed between said pressure sensing means and the main interior space for communicating said pressure to said pressure sensing means, means for shielding said offset portion of the chamber from the flow of air along said flow path through the main interior space, said shielding means providing an opening which faces downstream of the direction of said flow path, data processing means having input means for a measure of air pressure sensed by said sensing means, said data processing means deriving from the pressure values sensed, at least one parameter relating to the respiratory performance of the subject.

2. Apparatus according to claim 1 wherein a restricted passageway is provided between said offset portion of the chamber and said main interior space through which the flow of air passes.

3. Apparatus according to claim 1 wherein said offset portion of the chamber includes a projection disposed on one side of said end wall which is opposite from said main interior space.

4. Apparatus according to claim 1 further comprising a member displaceable by the pressure of air flow into the chamber and means operable by said member for recording the maximum displacement of said member to indicate mechanically the peak exhalation pressure of the subject.

5. Apparatus according to claim 1 having an outer casing comprising a plurality of separable parts and means for detachably securing said parts together, said parts having a junction between them when they are assembled together, said data processing means comprising electrical circuit means mounted on one or more of said parts adjacent said junction.

6. Apparatus according to claim 1 wherein said at least one parameter is selected from the following:
   (i) peak exhalation flow rate
   (ii) volume of air exhaled over the sampling time
   (iii) volume of air exhaled in the first second of exhalation.

7. Apparatus according to claim 1 wherein the data processing means comprise means for averaging a series of stored values during operation and for outputting an average value when said value exceeds the initial average value stored during said operation, whereby to indicate a peak exhalation pressure.

8. Apparatus according to claim 1 wherein the data processing means comprise means for integrating flow pressure values to indicate exhalation volume values.

9. Respiratory test apparatus comprising a chamber having a main interior space defined between an end wall and a piston, an entry conduit communicating with said main interior space for air to be blown by a subject into the chamber through said conduit, an outlet from the chamber permitting said air blown into said main interior space to escape therefrom at a restricted rate, pressure sensing means for providing a measure of air pressure, a portion of the chamber which is shielded fro mthe flow of air through said main interior space being disposed between said pressure sensing means and the main interior space for communicating said pressure to said pressure sensing means, data processing means having input means for a measure of air pressure sensed by said sensing means, said data processing means deriving from the pressure values sensed, at least one parameter relating to the respiratory performance of the subject wherein the end wall has at least one openign through which the air enters from said entry conduit and a collar connected to said end wall which extends into said main interior space away from said opening for shielding said portion from the flow through said space.

10. Apparatus according to claim 9 wherien said collar is in the form of a tubular extension projecting from said end wall into said main interior space.

11. Respiratory test apparatus comprising a chamber having a main interior space defined between an end wall and a piston, an entry conduit communicating with said main interior space for air to be blown by a subject into the chamber through said conduit, an outlet from the chamber permitting said air blown into said main interior space to escape therefrom at a restricted rate, pressure sensing means for providing a measure of air pressure, a portion of the chamber which is shielded from the flow of air through said main interior space being disposed between said pressure sensing means and the main interior space for communicating said pressure to said pressure sensing means, data processing means having input means for a measure of air pressure sensed by said sensing means, said data processing means deriving from the pressure values sensed, at least one parameter relating to the respiratory performance. of the subject, a member displaceable by the pressure of air flow into the chamber and means operable by said member for recording the maximum displacement of said member to indicate mechanically the peak exhalation flow rate of the subject wherein the chamber has a passage provided with at least one opening and a support extends through the opening from said end wall for sliding support of said member, said passage forming a shielding wall for shielding said portion of the chamber extending from said end wall into said main interior space, said shielding wall having a tubular configuration and surrounding said support at a spacing therefrom.

12. Respiratory test apparatus comprising a chamber having a main interior space defined between an end wall and a piston, an entry conduit communicating with said main interior space for air to be blown by a subject into the chamber through said conduit, an outlet from the chamber permitting said air blown into said main interior space to escape therefrom at a restricted rate, pressure sensing means for providing a measure of air pressure, a portion of the chamber being shielded from the flow of air through said main interior space and having an opening which faces downstream of the direction of said flow of air, the shielded portion of the chamber thereby being subjected to air pressure independent of the rate of flow of air through the chamber, said shielded portion of the chamber being disposed between said pressure sensing means and the main interior space for communicating said pressure to said pressure sensing means, data processing means having input means for a measure of air pressure sensed by said sensing means, said data processing means deriving from the pressure values sensed, at least one parameter relating to the respiratory performance of the subject.

* * * * *